(12) United States Patent
Nikolich

(10) Patent No.: US 6,876,902 B2
(45) Date of Patent: Apr. 5, 2005

(54) AUTOMATED SUPPLY CART AND SYSTEM

(76) Inventor: Aleks D. Nikolich, P.O. Box 11639, 4465 No. Oakland Ave. - Suite 303, Milwaukee, WI (US) 53211

( * ) Notice: Subject to any disclaimer, the term of this patent is extended or adjusted under 35 U.S.C. 154(b) by 0 days.

(21) Appl. No.: 10/077,732

(22) Filed: Feb. 19, 2002

(65) Prior Publication Data

US 2003/0158627 A1 Aug. 21, 2003

(51) Int. Cl.[7] .............................................. G06F 17/00
(52) U.S. Cl. ....................... 700/242; 700/236; 700/237; 700/244
(58) Field of Search ............................... 700/231, 232, 700/236, 237, 241, 244, 242; 705/28

(56) References Cited

U.S. PATENT DOCUMENTS 4,783,740 A * 11/1988 Ishizawa et al. .............. 705/28
5,805,455 A * 9/1998 Lipps .......................... 700/231
5,869,820 A * 2/1999 Chen et al. ................... 235/376
6,116,461 A * 9/2000 Broadfield et al. ............. 221/7
6,151,536 A * 11/2000 Arnold et al. ............... 700/237
6,272,394 B1 * 8/2001 Lipps .......................... 700/231

* cited by examiner

Primary Examiner—Gene O. Crawford

(57) ABSTRACT

The apparatus includes a storage cart in a storage area and supply carts in user areas at substantial distances from the storage area. The user carts are constantly open, and accessible to anyone, for a user to actuate to register on a computer unit the articles that are placed in and removed from the bins in the supply carts. The apparatus includes supplemental units detachably applied to the supply carts, having push-buttons corresponding to the bins in the supply carts. A running tally of the articles placed in and removed from the supply carts is maintained in a computer monitor by simple steps made by the user in so placing the articles in and removing them from the supply carts, without a separate operation for counting the articles.

15 Claims, 4 Drawing Sheets

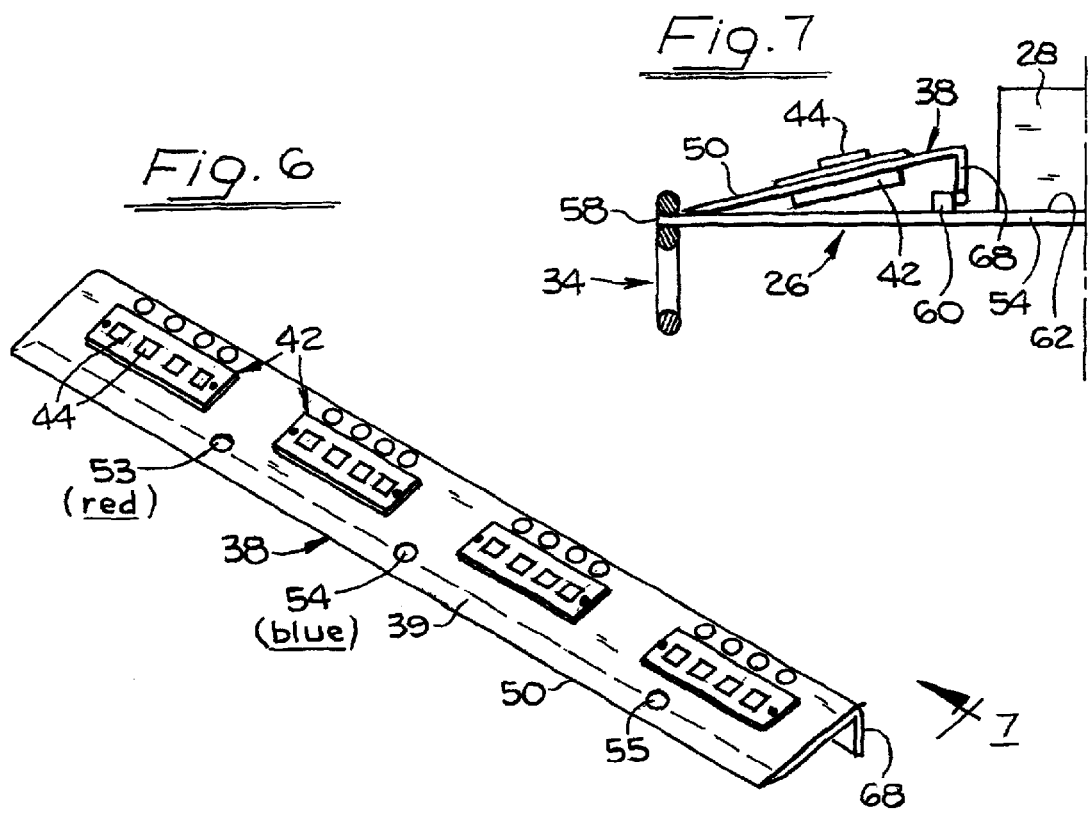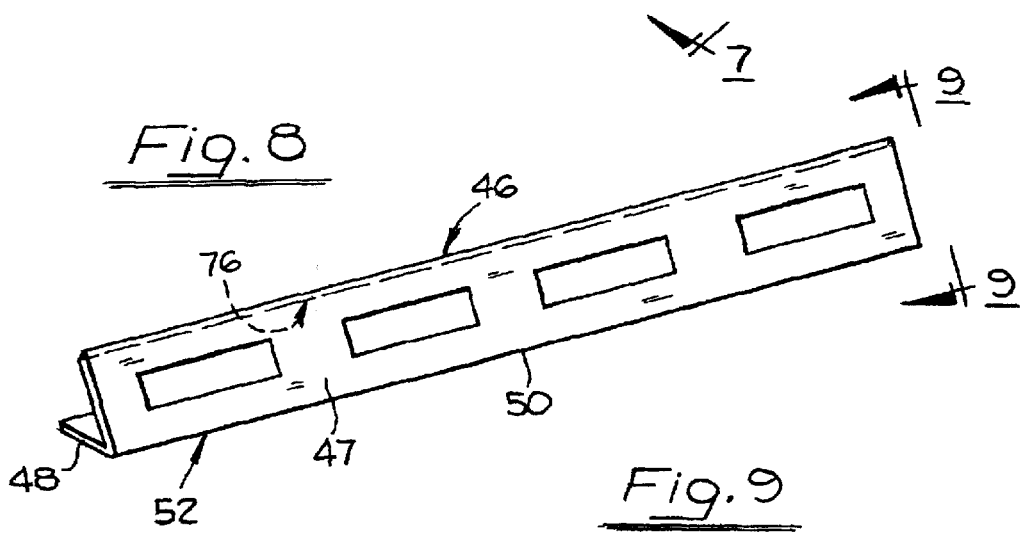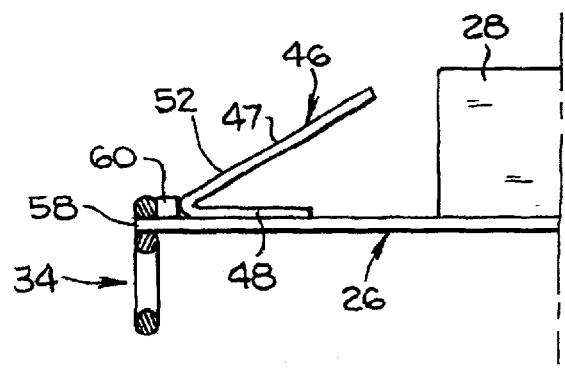

AUTOMATED SUPPLY CART AND SYSTEM

FIELD OF THE INVENTION

The automated supply cart of the invention may be used in any of a variety of businesses. Typical examples of such businesses are hospitals, offices, manufacturing plants, etc. All such fields of activity involve the use of supplies or parts for use in actual manufacturing, or in activities occurring in various businesses. In most such businesses, the parts and supplies utilized are normally located in a central storage area. As there items are used up, at the points of actual use or activity, it is necessary to supply those parts or items from the central storage area to the points of use.

When a business is small, transporting the items to the points of use is not a big factor, but as the businesses grow, it is necessary, or at least more efficient, to transport the items from the central storage area to supply carts that are distributed throughout the plant, and near the points of use.

Examples of items or supplies, are pens and pencils in offices, bandages and syringes in hospitals, electrical components for circuit board manufacturers. As businesses grow, and increase in size, it becomes necessary to provide these supplies near the areas of activity to improve the efficiency of their operations. This is typically accomplished by providing carts that are stocked with often-used supplies and placing them near the areas of activity. This results in diminishing the need to travel to and from the central storage area. A feature of great importance is the assignment of a "receiver" to each item that is taken from a supply cart. In healthcare, it is a patient who is receiving an item, such as a gauze bandage, or a roll of tape. In an office setting, this could be a department or individual who is receiving a box of pens. In manufacturing, for example, it may be an engine assembly that is receiving a manifold gasket.

As an overall phase of distributing supplies, supply carts used together with a central storage area have been used, but they have not been completely successful, and the supply carts and use thereof in the present invention provide great advantages over the arrangement of that phase known heretofore. The supplies of items and their distribution heretofore required manual counts of the items and further manual manipulations for entering various data into the system which included running tabulations of the items to be distributed.

Supply carts heretofore used have been of the kind known as closed carts, but the device and apparatus of the present invention includes open carts, and ready access thereto by various workers.

BRIEF DESCRIPTION OF THE INDIVIDUAL FIGURES OF THE DRAWINGS

FIG. 6 is a perspective view of a panel incorporated in the construction of the present invention that includes control buttons and indicators.

FIG. 7 is a fragmentary view of a supply cart with constructional features for horizontal mounting devices of the present invention on carts of known kind, and oriented according to line 7—7 of FIG. 6.

FIG. 8 is a view similar to FIG. 6 showing a panel of slightly different construction from that of FIG. 6.

FIG. 9 is a view taken at line 9—9 of FIG. 8 and including the form of FIG. 8, for vertical mounting.

Figure 1:
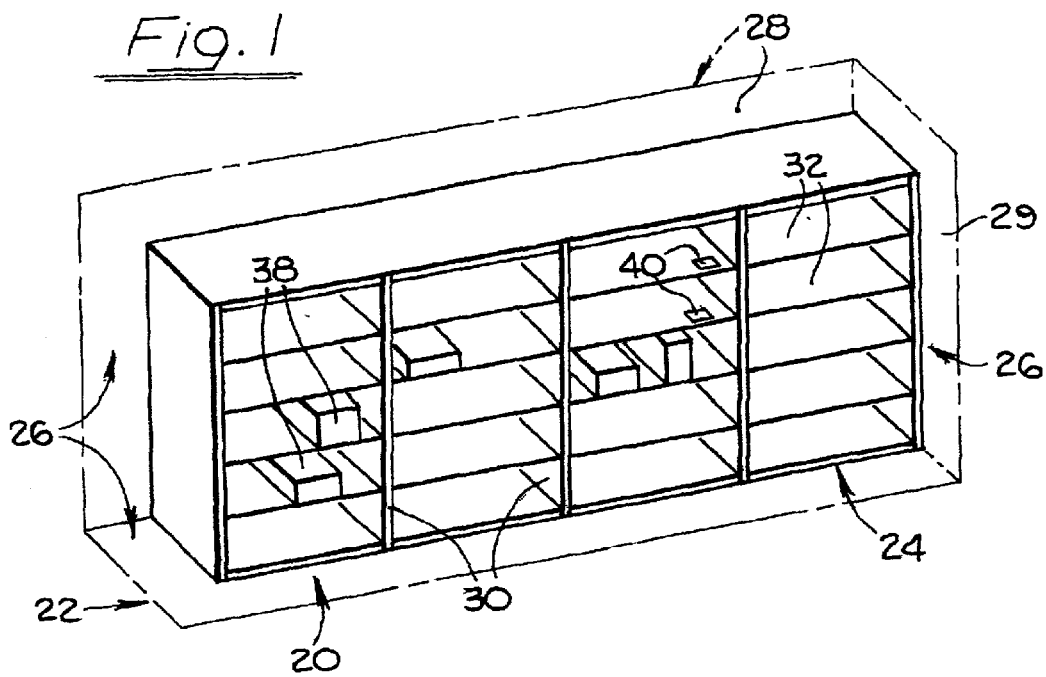
FIG. 1 shows in semi-diagrammatic form, a cart used in the central storage area.

An area of great importance is the assignment of a receiver to the items taken from a supply cart. In the case of healthcare, this is a patient who is receiving certain items under the direction of a nurse and it may be a gauze bandage or a roll of tape. In an office setting, for example, it could be an individual or a department receiving a box of items. In manufacturing it may be an engine assembly that is the actual receiver, requiring for example a manifold gasket. Information concerning the items and the receivers is important for maintaining full and complete records. For example, it may be desired to make charges for items given to a patient in a hospital; it may be well utilized in a manufacturing operation for controlling quality of the end product; it might be utilized in tracking various items used in manufacturing operations. Heretofore, in maintaining records of such steps, it was necessary to make manual counts of the items on the supply carts. Then other operators may enter this information manually into an inventory control system for use in replenishing the cart. Such steps were extremely labor-intensive. For instance, in medical supply cart may have 100 of certain items and upon use of these items, the supply is correspondingly depleted and the operation for maintaining the carts in fully supplied condition may require from one to two hours, if done thoroughly. In the system utilized heretofore, if a bin containing a specific supply of items is moved, it becomes very difficult to monitor the item. This is because most count forms rely on supplies always being in the same position. The present invention overcomes such difficulties.

Furthermore, in previously known systems, handwritten notes were made for entering into a computer for billing, or for other purposes; the labels are pulled off items and placed on cards that contain the names of the receivers, and heretofore this data was subsequently entered into a computer for billing and quality control purposes, which include additional manual steps.

These steps result in great inefficiency. In an average size hospital of up to 300 beds, there may be anywhere from 20 to 30 medical units in the hospital that had dedicated supply carts, i.e., used in certain selected areas in the hospital.

As indicated above, the various items are provided with removeable labels, which include the inventory number for the item. When the item is taken from the supply cart by a caregiver, the label is removed from the supply before the item is dispensed and affixed to a form containing a patient's name. These forms are normally located near the medical unit's secretary or nurse's station. The unit's secretary then has the laborious task of entering all the patient charges into the computerized billing and inventory systems. These steps require additional time beyond the mere steps of picking the items from the supply cart. Furthermore, it has often happened that caregivers would forget to apply the labels to patient forms, and by accident they may be lost.

DETAILED DESCRIPTION OF THE DRAWINGS

The drawings are, in great part of semi-diagrammatic nature because the carts shown therein are different from each other mainly in details, and represent various carts that are now on the market. Accordingly, a description of the details of the carts will be held to a minimum.

Supply carts are in the form of devices that are normally stationary, each consisting of, for example, a set of shelves mounted on posts, but they can be moved for relocating them. FIG. 1 shows a central storage cart 20, located in a general storage area 26, roughly defined by wall elements 28, 29 and located, for example, in the basement of a building, or any other desired central location.

Figure 2:
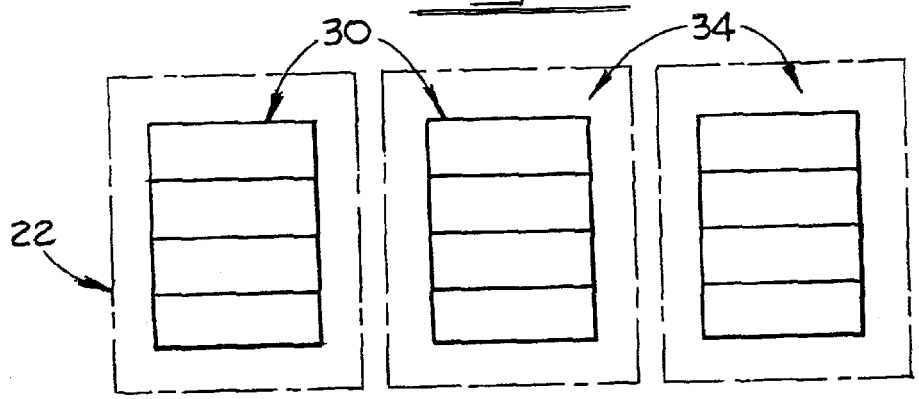
FIG. 2 is a semi-diagrammatic front view of a plurality of supply carts.

The cart 20 includes posts 30 and a series of shelves 32. These posts and shelves may be of any desired detail form FIG. 2 shows automated supply carts 34, generally similar to the storage cart 20, but differing in detail as described below.

Figure 3:
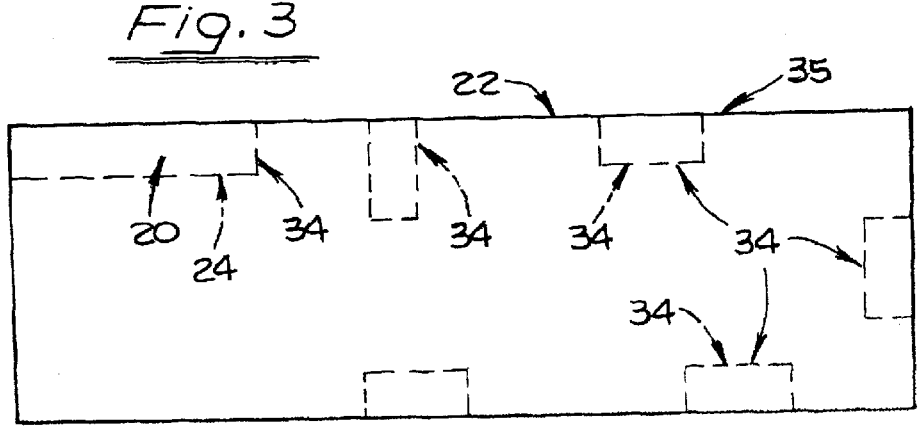
FIG. 3 is a semi-diagrammatic view of a plant or building in which the apparatus and system of the present invention is utilized, showing different locations of the supply carts, all at a distance from the main storage area and generally nearer the periphery of the plant or building.

FIG. 3 is a plan view showing the storage cart 20, and the supply carts 34 in distributed locations in a building or plant 35 in which they are used. A plurality of automated supply carts 34 are located at various positions at the periphery of the building, and it is to be noted particularly that they are of substantial distance from the storage area, within the spirit of the present invention. The supply carts in this figure are located adjacent areas of medical units in which the receivers are located.

While the apparatus of the present invention is applicable to a previously known system, the invention can of course be incorporated in the original construction of supply carts.

Figure 4:
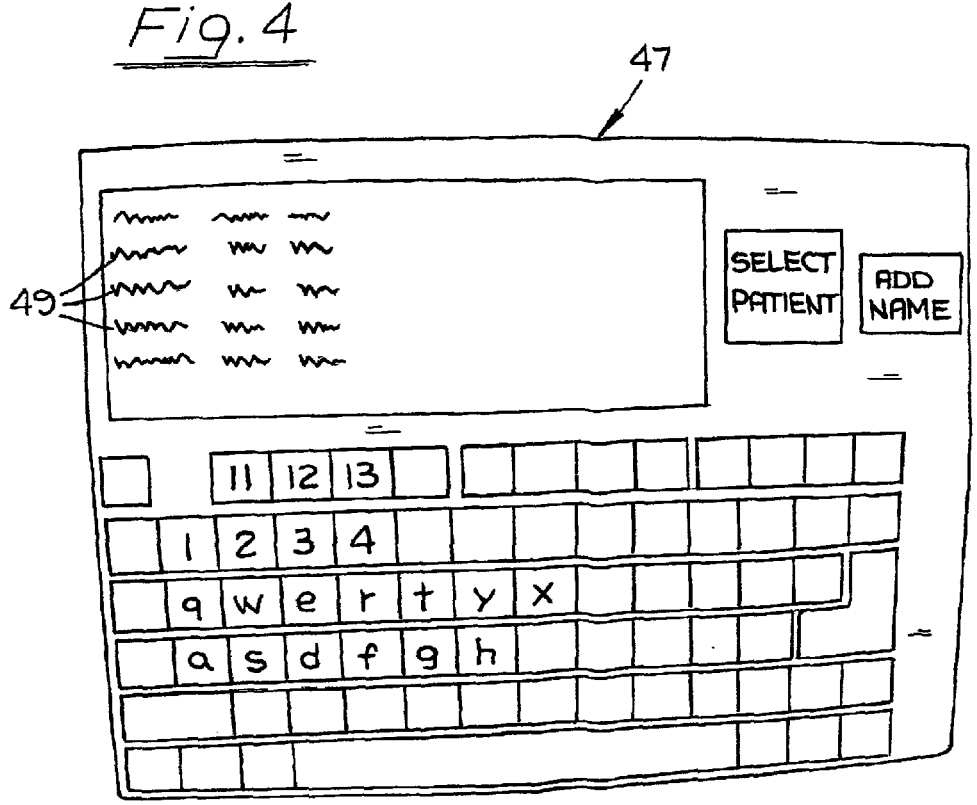
FIG. 4 is a face view of a monitor screen

According to the invention the supply carts 34 are fitted with buttons 44 (FIG. 10) that have indicated corresponding to individuals bins 36 in the carts. Each bin is labeled with a cart number 37 (FIG. 10), a shelf number 39 and a bin number 40. (FIG. 1) This identifies its position in the supply cart. If a bin or cart is moved, it can be easily placed back into the proper position by examining the location indicated on its label. When at item is obtained from a bin, a corresponding button 44 (FIG. 10) is pressed to indicate that the item has been taken. The cart computer or monitor (FIG. 4) displays the selected item at 49 on the monitor for information purposes. If the item contains a hazardous material, such as latex, the system provides an audible alert and displays 51, 52 (FIG. 10) a warning. If latex, the current selection, is not desired any longer, then the operator pushes the cancel button 53 (FIG. 6), signified by a red 'X' which will eliminate the action. If an item is to be returned, the "add" button 54 (FIG. 6), signified by a blue '+', is pressed, followed by the button 44 that represents the item being returned. If a user wishes to indicate that a bin is empty an 'empty bin' button 55 is pressed, followed by the button of the supply item. When a bin is emptied, the indicator associated with that emptied item is activated. The features of the apparatus of the present invention produce unusual and effective results. The apparatus is useful in a hospital setting where the inventory level of a particular item is decremented each time its button is pressed. When the level drops below a specified level, an order is made by the system to replenish the item. The apparatus also provides an audible and visual alert 56, 57 (FIG. 10) when supplies containing hazardous materials are removed from the cart.

The apparatus as just described, is operable for replenishing bins once they are empty. In this case, an item's button can signify that the entire bin needs to be replenished.

The apparatus includes a server computer and a cart computer and periodically, the server computer contacts the cart computer (or vice versa) and collects the current status of the cart, controlled by the cart computer. The server computer maintains a database of the current inventory on each cart, safety stock levels and par levels. The computer indicates the levels of items in the supply carts: (a) par levels, (b) current inventory levels, and (c) safety levels. The computers generate a "pick list" for use by a person to maintain the desired level in the carts. When the current inventory level of an item reaches a safety stock level, the server computer indicates that the item must be replenished by two methods. First, the server computer can send a message to the hospital's inventory control system, indicating that the bins should be restocked. This may be accomplished by sending a message directly to the inventory control system, or by emulating the communications of a portable computer that was formally utilized to submit the count. Second, the server computer can generate a printed pick list with a unique alphanumeric code that indicates what items should be replenished. After the items on the pick list are placed on the cart, the cart's inventory levels can be adjusted by entering the unique alphanumeric code into the cart computer.

In the apparatus of the present invention, user or receiver names are displayed on the touch screen 47 having buttons and inscriptions 49, which is done through a software interface with the hospital's census system In the operation and use of the apparatus of the present invention, a user of the supply cart and system, simply touches the desired receiver on the screen to identify the receiver. Subsequently, items are manually taken from the supply cart and their respective buttons pressed. The monitor 47 then displays the item that had been selected. When the transaction is complete, the system sends the order with the patient name and item for processing by the server computer. The server computer adjusts the cart inventory and sends messages to the facility's billing computer and inventory control computer.

In manufacturing operations, and similar operations, the steps and combination of steps are substantially the same as in the case of the hospital. New advantages and functions of the apparatus of the present invention, as set out in the foregoing: inventory control is integrated into the step of taking an item; inventory levels are monitored in real-time; the items are left undisturbed from their pre-automation state. This allows caregivers to continue to take items from their traditional locations; items are easy to access—heretofore supply cart systems store the supplies in locked cabinets and drawers and must be under the control of another person, other than those operating the supply carts, and the healthcare givers.

Heretofore, in effecting a continuous and proper flow of articles, to assure that the supply carts are fully stocked, hospital personnel frequently monitor the inventory levels on the cart. As a first step, all the remaining items in each of the supply carts are manually counted. This step was very time-consuming since typical supply carts contain over 100 individual items. The count is submitted to the hospital's inventory control system either by entering the count into a portable hand-held computer that interfaces with the main inventory control system, or by entering the count directly into the main inventory control system through a stationary computer. The inventory control system takes the difference between the par level (i.e. fully stocked level) and current inventory level for each item, and generates a pick list that contains the item's name and calculated difference in those numbers. Hospital personnel use the pick list to replenish the supply carts from their central storage stock. As a result, heretofore many hospitals have had dedicated personnel that only count and restock supplies in medical supply carts.

The automated supply and replenishment in the supply carts results in automatic security, i.e., the records of the items in stock in the supply carts are brought up to date on each item, and therefore a security camera would function to catch every maneuver or step in the user of the supply cart. In the use of the apparatus of the present invention, a user, e.g., a health caregiver or nurse, selects an item and withdraws it, and may use the hand as used for withdrawing the item for pressing the corresponding button to register the event. This system has greater use participation, which leads to more accurate inventory counts in the system computer.

Another benefit of the system is the automatic recognition of items containing hazardous materials. In addition to the warning tape on the items label, the system emits an alert tone and displays a warning message when the button for the items is pressed. This feature gives caregivers and other users an extra level of protection from exposure to dangerous materials, such as latex.

Figure 11:
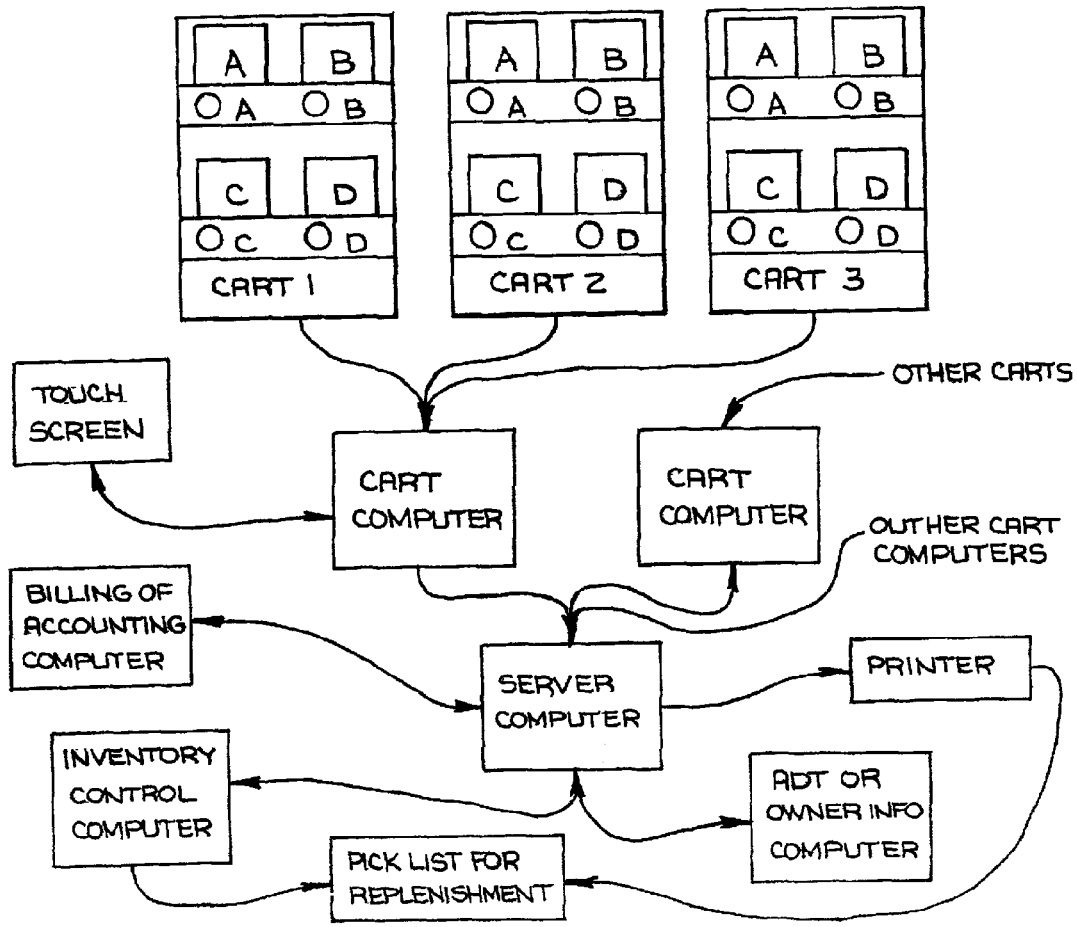
FIG. 11 is a block diagram of controls utilized in the system of the invention.

The flow chart of FIG. 11 shows a plurality of supply carts. Each supply cart includes a component for registering the items selected from the supply cart and transmits the result to the corresponding cart computer. Therefore, a plurality of supply carts may be utilized with a single computer, and the results of signal transmission therebetween is further transferred to the server computer for total inventory of the entire operation, such as a hospital.

The server computer calculates the difference between these numbers and transmits a signal of the pick list to the printer which prints a list of the items for which there is a number of supply items less than the par level. All of the cart computers transmit signals to the computer server, and the computer server transmits these signals to the printer, and the signals in turn are transmitted to the pick list unit. This is done for each of the carts.

Figure 5:
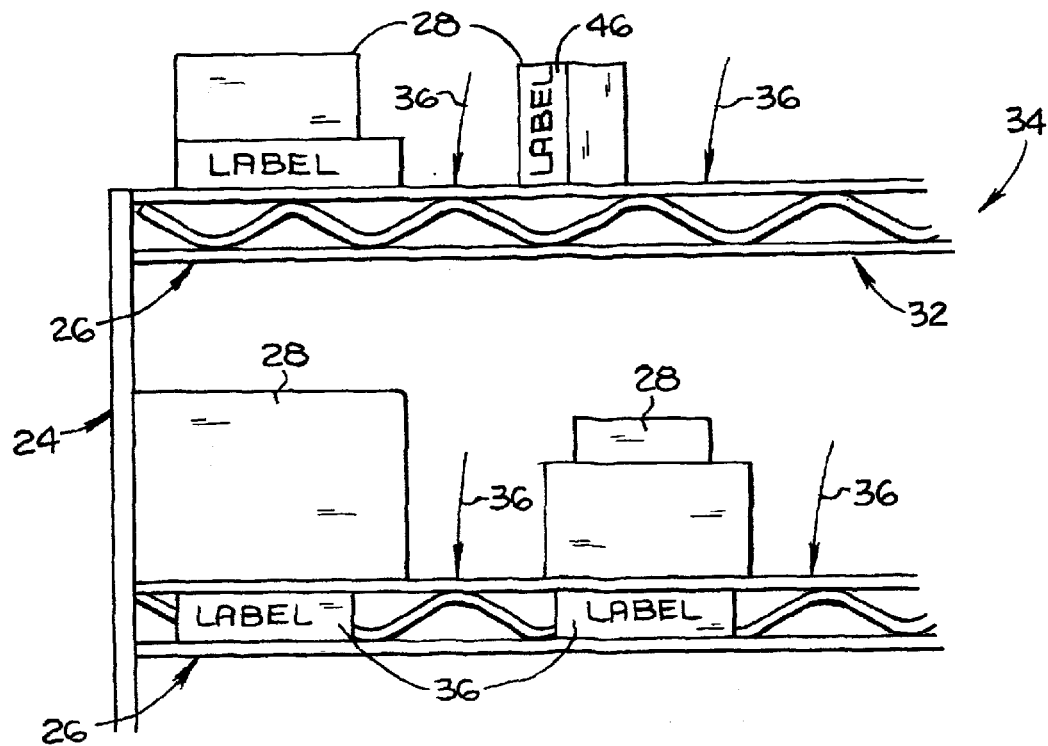
FIG. 5 is a fragmentary view, on an enlarged scale, of one of the supply carts.

Reference is again made to FIG. 5 showing a portion of a supply cart 34, and showing particularly portions of the shelves 32. (The bins 36 may be merely areas on the shelf, and on each area is a receptacle 38 in which the items to be distributed are contained, as indicated at 40. Each shelf 32 includes one or more panels 42 which may be of any desired length transversely of the cart. On the panel 42 are the push buttons 44 identifying articles in the receptacles or bins 38.

Figure 10:
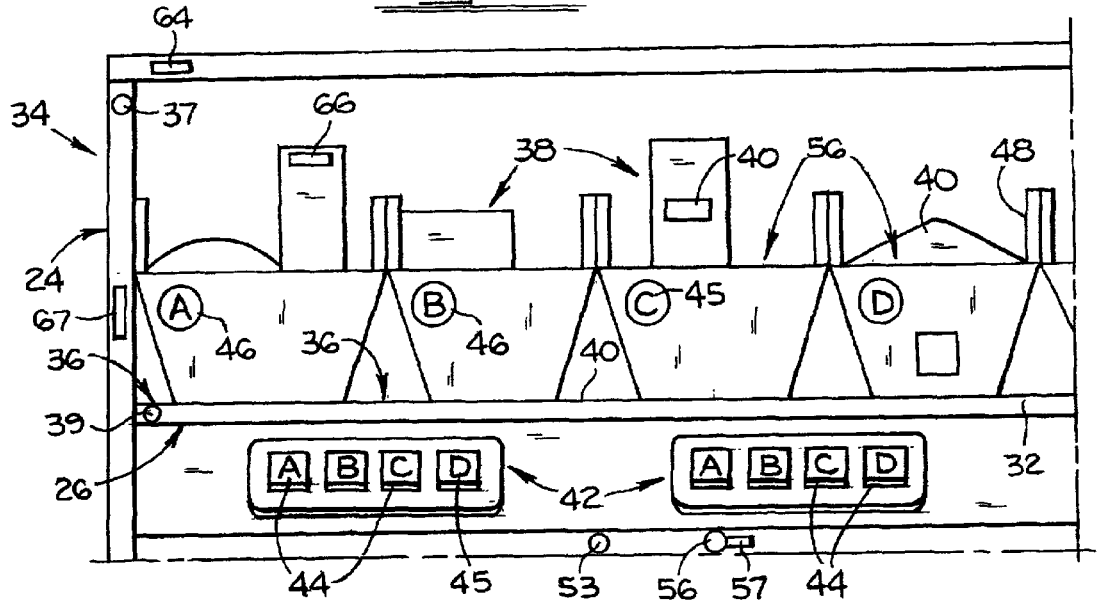
FIG. 10 is a view oriented according to FIG. 5 showing a greater portion of a cart than that of FIG. 5, and showing a plurality of bins therein.

These push buttons have identifying letters 45, which occur also on the article 56 (FIG. 10). Each of the articles 28 (FIG. 5) includes a label 46 identifying the articles in the bins 36. The user of the cart when withdrawing an article 28, depresses the corresponding button 44 to indicate the withdrawal of the corresponding article.

In FIG. 10 the bins 36 are provided with sidewalls 48 which may interengage, as between the bins, these walls serving to facilitate the limits of the bin areas 36. These FIGS. (5, 10) will be referred to again in the description below of the utilization of he various elements in using the system.

A great advantage of the invention resides in the feature that the apparatus thereof can be easily and readily applied to a shelf of known kind, without modifying either the shelf itself, or any of the structure of the device of the present invention. Concerning this feature, attention is directed to FIGS. 6–9. FIGS. 6 and 7 show a panel 50 and FIGS. 8 and 9 show a panel 52 which are very similar in construction but differ in details for accommodating detailed differences in the previously known carts to which they are applied. In the case of FIGS. 6 and 7, a supply cart 34 is shown, having a shelf 32 on which articles to be distributed, are positioned. The shelf has a front edge 58, and on the shelf is a rib 60 adjacent the inner or rear edge thereof (FIG. 7). The shelf has a top surface 62 on which the panels 50, 52 are disposed. The panel 50 includes a continuous board with a vertical cleat 68. The panel is fitted over the shelf 32, covering the old panels 44, with the cleat 68 fitted behind, or inwardly of, the rib 60, retaining the panel 50 on the shelf. This exposes the push buttons 42 on the panel 50 for access by the user.

In the case of FIGS. 8, 9, the panel 52 has a continuous board 47, with a cleat 48 secured to the lower edge of the board. The panel 52 is applied to the shelf as shown in FIG. 9, with the lower edge of the board fitted against the rib 60 at he front edge of the shelf. The panel then rests against the rib and is prevented from sliding off the shelf. In each case, in using the panels 50, 52, the main board 39 or 47, is disposed at an angle for easy view by the user.

The panels 50, 52 are thus constructed and arranged on vertical mounts on the cart.

It will be appreciated that the push buttons on the panels 50, 52 are used in calculations of the system as referred to below. In each of the panels 50, 52 there are electrical circuits, indicated by the electrical conductors 76 (FIG. 8) for use in performing calculations in the main electrical circuit (FIG. 11) referred to below.

The push buttons in the panels 50, 52, bear the identification of the various items to be distributed. In the beginning, the supply carts are filled to capacity, that is, each of the shelves, and/or bins, is filled to capacity. The bins or shelves are designed to hold a predetermined number of articles, such for example as, 50, 100, 150, etc. The maximum number of items in each bin is known as par, and as the articles are used, there is of course a lesser number in each of the bins and this number is known as inventory level. The minimum number of items designated for each bin is known as the safety level. This number is that which the bin must have for the operation to be performed, and the number should not fall below that level.

It is important that the ownership of the items to be distributed be incorporated in the system. In the case of the hospital, for example, a patient would be the receiver or owner, this indicating the final point of distribution. A nurse, for example, knowing the needs of the patient, approaches the corresponding open supply cart and withdraws the item desired. In this operation, she also pushes the corresponding push button, identifying the item by bin number, to enter the proper signal in the system. The cart computer that is connected to multiple supply carts records this button press and relays the information to the server computer. The server computer maintains a database of current inventory levels at each cart, safety stock levels and par levels. When the inventory level in a bin reaches a safety stock level, the server computer sends a message to the inventory control system indicating that the bins should be restocked. The restocking amount if the difference between the par and safety stock levels. If an inventory control system is not computerized, the server computer can generate a printed pick list that indicates what items should be replenished.

If ownership assignment is desired, then it is necessary to create a means in which to identify the owner. For hospitals this can be accomplished by implementing a touch-screen kiosk system that interfaces with the hospital's ADT (Admitting, Discharge, Transfer) system, or communicate with a device that contains the receiver's identification (i.e. bar code, radio frequency, identification tag, infrared tag, etc.).

Another feature is the provision of monitoring for indicating whether the bins are empty. Light indicators 62 (FIG. 7) are provided, related respectively with the bins in the electrical circuit to indicate when the bins are empty, allowing the users to notice immediately whether an empty bin was reported to the system. Scanners 64 (FIG. 10) of desired type, e.g. bar code, magnetic strip, radio frequency identification, are provided at each cart, or group of carts to uniquely identify the user. This enables more than one user to pick items within the supply area controlled by the system. For instance, Nurse A can pick items for Patient B, and Nurse C can pick items for Patient D, within the same supply cart. The user can automate the adjustment of inventory levels at the supply cart through the use of a unique pick list identification code. After replenishing the cart with items located on a pick list, the user submits the unique pick list identification code to the computer, at 66 and 67 (FIG. 10), controlling the supply cart. This is important in situations where items are picked in the warehouse, but not placed on the supply cart until much later.

I claim:

1. A method for distributing a plurality of articles of different kinds, comprising the steps, providing a storage area and a cart in the storage area, the storage cart having a plurality of bins for supporting and identifying said articles, providing a plurality of receiver areas at substantial distances from the storage areas and the receiver areas being adapted to be occupied by receivers capable of receiving said articles, providing a plurality of supply carts at distributed locations, the supply carts having bins respectively identical with the bins in the storage cart and having indicia identifying said articles put therein, the supply carts being open and thereby enabling any person to withdraw articles therefrom and transport them to the receiver area, providing supplemental panels having manually actuated means for registering articles placed in and withdrawn from the supply bins, manually actuating the registering means, and utilizing a computer means to register the difference in the predetermined full stocking level of the supply bin and the number of articles in the supply bin, and utilizing a computer means to register the difference in the said difference and the number of articles in its respective storage bin.

2. A method according to claim 1 and providing a security camera and utilizing it for operably photographing the supply cart throughout said predetermined period of operation of the supply cart.

3. A method according to claim 1, and including the steps, utilizing a bar code reader as an auxiliary means of registering articles placed in and withdrawn from the bins.

4. A method according to claim 1, and including the steps, utilizing a radio-frequency (RF) identification reader as an auxiliary means of requesting articles placed in and withdrawn from the bins.

5. A method according to claim 1, and including the steps, utilizing an infrared (IR) reader as an auxiliary means of requesting articles placed in and withdrawn from the bins.

6. A method according to claim 1, and including the steps, submitting a charge event to a billing system when a user is identified and an article is withdrawn from a bin.

7. A method according to claim 1, and including the steps, submitting an assignment event to a manufacturing management system when a user is identified and an article is withdrawn from a bin.

8. A method according to claim 1, and including the steps, maintaining the supply cart in open condition indefinitely, withdrawing articles continuously throughout a predetermined overall period, independently of operation of other steps, and restocking articles from the storage cart through the supply cart, independently of other steps.

9. A method according to claim 8 and including the steps of providing a single such storage cart, and a plurality of such supply carts at locations at substantial distances from the storage cart and from each other, and utilizing each supply cart independently from each other for registering said differences.

10. A method according to claim 1, and including the steps, utilizing an auxiliary keypad as an auxiliary means of requestin articles placed in and withdrawn from the bins.

11. A method according to claim 1, and including the steps, utilizing a bar code reader as an auxiliary means to identify the users of the articles withdrawn.

12. A method according to claim 1, and including the steps, utilizing a radio-frequency (RF) identification reader as an auxiliary means to identify the users of the articles withdrawn.

13. A method according to claim 1, and including the steps, utilizing an infrared (IR) reader as an auxiliary means to identify the users of the articles withdrawn.

14. A method according to claim 1, and including the steps, utilizing an auxiliary keypad as an auxiliary means to identify the users of the articles withdrawn.

15. Apparatus for use in distributing a plurality of articles of different kinds throughout a facility that has a central storage area, and a plurality of user areas distributed in the facility at substantial distances from the storage area, comprising, a storage cart in the storage area having a plurality of storage bins for holding a corresponding number of said articles of different kinds, an open supply cart adjacent to each of the user areas and having supply bins for receiving and holding said articles, and the supply cart having labels individually identifying articles in the supply bins, supplemental panels having push buttons operably associated with the supply bins, the apparatus including a computer for registering signals from the push buttons, the computer being operably associated with each supply cart, and operable in response to actuation of the push buttons in the respective supplemental panel for recording the withdrawing of articles from and the placing of articles in the supply bins, and including means for providing alert signal in response to the presence of hazardous materials in the articles.

* * * * *